United States Patent [19]

McFarland

[11] Patent Number: 4,973,793

[45] Date of Patent: Nov. 27, 1990

[54] OXIDATIVE DEHYDROGENATION OF AMYLENES

[75] Inventor: Cecil G. McFarland, Houston, Tex.

[73] Assignee: Texas Petrochemicals Corporation, Houston, Tex.

[21] Appl. No.: 363,591

[22] Filed: Jun. 8, 1989

[51] Int. Cl.$^5$ .......................... C07C 5/09; C07C 5/327
[52] U.S. Cl. .................................. 585/658; 585/621; 585/625
[58] Field of Search .................... 585/621, 625, 658

[56] References Cited

U.S. PATENT DOCUMENTS

| | | | |
|---|---|---|---|
| 3,207,809 | 9/1965 | Bajars | 260/680 |
| 3,274,283 | 9/1966 | Bethell et al. | 585/658 |
| 3,291,854 | 12/1966 | Bajars | 260/680 |
| 3,303,235 | 2/1967 | Croce et al. | 585/657 |
| 3,303,237 | 2/1967 | Croce et al. | 260/680 |
| 3,342,890 | 9/1967 | Croce et al. | 585/625 |
| 3,374,283 | 3/1968 | Bajars | 260/680 |
| 3,660,513 | 5/1972 | Davison | 260/680 |
| 3,852,369 | 12/1974 | Walker et al. | 585/658 |
| 3,870,764 | 3/1975 | Gichowski et al. | 260/680 |
| 3,897,369 | 7/1975 | Bertus | 252/469 |
| 3,931,351 | 1/1976 | Hinkson et al. | 585/657 |
| 3,933,933 | 1/1976 | Bertus | 260/680 |
| 3,951,869 | 4/1976 | Baker | 252/471 |
| 3,998,760 | 12/1976 | Christmann et al. | 252/471 |
| 4,108,918 | 8/1978 | Hoppstock et al. | 260/680 |
| 4,332,972 | 6/1982 | Christmann et al. | 585/442 |
| 4,336,409 | 6/1982 | Yamamoto et al. | 585/621 |
| 4,658,074 | 4/1987 | Bajars et al. | 585/380 |
| 4,658,080 | 4/1987 | McFarland | 585/658 |

*Primary Examiner*—H. M. S. Sneed
*Assistant Examiner*—James Saba
*Attorney, Agent, or Firm*—Kenneth H. Johnson

[57] ABSTRACT

Cofeeding butylenes with amylenes in a catalytic oxidative dehydrogenation reaction substantially improves the conversion of the amylenes. The approved amylene conversion is obtained by the oxidative dehydrogenation of mixtures of amylenes and from 10 to 95 mole % butylenes.

21 Claims, No Drawings

OXIDATIVE DEHYDROGENATION OF AMYLENES

BACKGROUND OF THE INVENTION

1. Field of the Invention

This invention relates to a process for dehydrogenating hydrocarbons. More particularly, this invention relates to the oxidative dehydrogenation of amylenes, particularly isoamylenes in the presence of metal ferrite catalyst compositions.

2. Description of the Prior Art

Oxidative dehydrogenation processes wherein metal ferrite catalyst compositions have been employed to convert saturated and/or unsaturated hydrocarbons to more highly unsaturated hydrocarbons through removal of hydrogen from such hydrocarbons are known in the art. See, for example, U.S. Pat. No. 3,303,235. U.S. Pat. No. 3,660,513 to Davison discloses the production of isoprene by the oxidative dehydrogenation of $C_5$ olefins in a $C_5$ refinery cut containing 97% olefins, less than 1% $C_4$'s and about 2% others in the presence of an iron phosphate catalyst, steam and oxygen. Generally the amylene conversion has not been as favorable as, for example the conversion of butenes to butadiene. It is an advantage of the present invention that amylene conversion is substantially increased. It is a further advantage that using the present process isoprene can be manufactured in commercial equipment used for the manufacture of butadiene.

SUMMARY OF THE INVENTION

Briefly the present invention is a process for the oxidative dehydrogenation of aliphatic hydrocarbons having five carbon atoms comprising contacting a mixture of $C_5$ aliphatic hydrocarbons and from 15 to 95 mole % $C_4$ hydrocarbons based on the total $C_5$ and $C_4$ hydrocarbons (preferably at least 20 mole % up to 80 mole % $C_4$'s) with an oxidative dehydrogenation catalyst in the presence of oxygen and steam, for example, cofeeding butylenes with amylenes in a catalytic oxidative dehydrogenation reaction substantially improves the conversion of the amylenes.

In accordance with the present invention, a process is provided for the oxidative dehydrogenation of mixtures of amylenes and butylenes which comprises contacting the mixture and oxygen in the presence of an oxidative dehydrogenation catalyst composition.

DESCRIPTION OF THE PREFERRED EMBODIMENTS

General

In accordance with the process of the instant invention, certain organic compounds are dehydrogenated to less saturated compounds of the same carbon number at elevated temperature in the presence of oxygen and an appropriate catalyst. Improved $C_5$ conversion is obtained by the oxidative dehydrogenation of mixtures of $C_5$ and $C_4$ aliphatic hydrocarbons, e.g., amylenes/butylenes containing at least 15 mole % butylenes, preferably at least 20 mole % butylenes, since only slight improvement in the conversion of amylenes can be expected at a butylene concentration of less than 20 mole percent. It was found that the conversion of amylenes to isoprene by oxidative dehydrogenation was substantially increased by having butylenes present. Generally butylenes in the amylene/butylene reaction feed are in the range of 30 to 95 mole %, preferably 40 to 80 mole %. In the ranges disclosed there is an observable improvement in the conversion of the $C_5$'s as the $C_4$ concentration in the reaction mix increases, however at $C_4$ concentrations in excess of 95 mole % there is little amylene in the reaction mix. Hence, the actual amount of isoprene recoverable from a stream containing less than 20 mole % amylenes (i.e. up to 80 mole % $C_4$'s) may not provide a commercially desirable process. Although there is a decline in selectivity to isoprene with increasing butylene concentration, the increase in the conversion of amylenes in the presence of butylenes, results in an improved yield of isoprene. However, some of the data suggest a more rapid decline in selectivity to isoprene at butylene concentrations greater than 80 mole %. The most preferred range of butylene concentration in the reaction mixture is from about 30 to 70 mole %, e.g. 50 to 70 mole %.

In a preferred process the amylenes comprise isoamylenes, viz., 3-methyl-1-butene, 3-methyl-2-butene and 2-methyl-1-butene and the product isoprene (2-methyl-1,3-butadiene).

In the instant process, the organic compound is dehydrogenated in the presence of oxygen. Oxygen may be fed to the reaction zone as pure oxygen, air, oxygen-enriched air, oxygen mixed with a diluent, and so forth. Oxygen in the desired amount may be added in the feed to the dehydrogenation zone and oxygen may also be added in increments to the dehydrogenation zone. The oxygen may be supplied in a cyclic manner such as described in U.S. Pat. No. 3,420,911.

The Catalyst

The catalyst generally in this invention contain iron, oxygen and at least one other metallic element and are crystalline compositions of iron, oxygen, and at least one other metallic element. The catalysts may be ferrites and/or spinels. The metallic elements, other than iron, of the catalysts can be varied widely.

The total number of atoms of the second metallic ingredient(s) should preferably be from about 0.05 to 2.0 total atoms per atom of iron and preferably will be from or about 0.20 to 1.0 total atoms per atom of iron, with a particularly preferred ratio of 0.35 to 0.6 total atoms per atom of iron.

A preferred type of catalyst of this type is that having a face-centered cubic form of crystalline structure. Examples of this type of catalyst are ferrites of the general formula $MeO.Fe_2O_3$, where Me is a divalent metal cation such as $Mg^{++}$ or $Ni^{++}$. However, if the cations are large, such as $Sr^{++}$ (1.35 A.u.), the spinel structure may not occur and other types of ferrites having a hexagonal crystal of the type $SrO.6Fe_2O_3$ may be formed. An additional example of a hexagonal ferrite is $PbO.6Fe_2O_3$. These hexagonal ferrites are within the scope of the definition of catalyst of this invention.

Suitable catalysts may also be ferrites wherein other metals are partially substituted for the iron. For example, $Al^{+++}$ or $Cr^{+++}$ or other atoms having a valence of +3 may be partially substituted for some of the $Fe^{+++}$ atoms Also, metal atoms having a valence of +4, such as $Ti^{++++}$ or $Ge^{++++}$ may replace some of the $Fe^{+++}$ ions. However, the catalysts will still suitably have iron present in an amount described above in relation to the total atoms of the second metallic ingredient(s). Thus, if the crystal contained, e.g., $Fe^{+++}$, $Cr^{+++}$, and $Mg^{++}$, the iron should still desirably be present within the ratios described, with the $Cr^{+++}$, and the $Mg^{++}$ being the second metallic ingredient (s) in this case.

It is not necessary that the catalysts contain all of the iron or the second metallic ingredient(s) in a crystalline structure. The catalysts may contain an excess of either iron or of the second metallic ingredient(s) over that which will form a crystalline structure. An example of this would be where magnesium ferrite contained or was combined with $Fe_2O_3$ or MgO.

The catalysts may have the iron combined in crystalline structure with oxygen and more than one other metallic element, as mentioned above. For example, a preferred type of ferrite is that essentially or approximately of the formula, $MeFe_2O_4$, where Me represents a divalent metal ion with an ionic radius approximately between 0.5 and 1.1 A.u., preferably between about 0.6 and 1.0 A.u. In the case of simple ferrites, Me may be, e.g., one of the divalent ions of the transition elements such as Mn, Co, Ni, Cu, Zn, Mg or Cd. However, a combination of these ions is also possible to form a ferrite such as $Ni_{0.5}Mg_{0.5}Fe_2O_4$ or $Ni_{0.25}Mg_{0.75}Fe_2O_4$. Moreover, the symbol Me may represent a combination of ions which have an average valency of two, for example, $Li_{0.5}Fe_{2.5}O_4$. However, it is essential that the crystalline structure contain a metallic element other than iron.

Example of catalysts are such as magnesium ferrite, cobalt ferrite, nickel ferrite, cupric ferrite, cuprous ferrite, zinc ferrite, barium ferrite, strontium ferrite, manganese ferrite, lithium ferrite, calcium ferrite, cadmium ferrite, potassium ferrite, sodium ferrite, lead ferrite, silver ferrite, zirconium ferrite, and rare earth ferrites such as cerium ferrite, or mixtures of ferrites, such as ferrites containing iron combined with at least one element selected from the group consisting of Mg, Zn, Ni, Co, Mn, Cu, Cd, Ca, Ba, Sr, Al, Cr, Ti, V, Mo, W. Na, Li, K. Sn, Pb, Sb, Bi, Ga, Ce, Th, other rare earth elements and mixtures thereof. Examples of mixed ferrites are magnesium ferrite plus zinc ferrite, magnesium ferrite plus nickel ferrite, magnesium ferrite plus cobalt ferrite, magnesium ferrite plus nickel ferrite plus zinc ferrite, magnesium ferrite plus manganese ferrite.

Although the catalysts may be broadly defined as containing crystalline structures of iron, oxygen and the second metallic ingredient(s), certain types of catalysts are preferred. Valuable catalysts were produced comprising as the main active constituent in the catalyst surface exposed to the reaction gases, iron, oxygen and at least one element from Group IIA, IIB or VIII of the Periodic Table such as those selected from the group consisting of magnesium, manganese, calcium, cadmium, cobalt, zinc, nickel, barium, strontium, and mixtures thereof. The Periodic Table referred to is the one on pages 400–401 of the Handbook of Chemistry and Physics (39th edition, 1957–8, Chemical Rubber Publishing Co, Cleveland, Ohio). The preferred catalysts are the ferrites. Preferred catalyst will have iron in the catalyst surface in an amount from 20 to 95, and preferably from 30 to 90 weight percent of the total weight of iron and the second metallic ingredient(s). However, with the individual catalysts the ratio of iron to the other elements of Group IIA, IIB and VIII will preferably be within certain ranges. For example, for magnesium catalysts, including magnesium ferrite, the catalysts will preferably have from 75 to 97 weight percent iron based on the total weight of iron and magnesium. Similarly, for the catalysts containing iron and one of the elements selected from the group consisting of calcium, cadmium and cobalt, the weight percent of iron will preferably be from 30 to 90 weight percent iron based on the total weight of iron and the calcium, cadmium and/or cobalt. For the zinc catalysts, including zinc ferrite, the weight percent iron will preferably be within the range of 20 to 95 weight percent with good results having been obtained with from about 51 to 80 weight percent iron based on the total weight of iron and zinc. For the catalyst containing strontium and/or barium, including strontium ferrite and barium including strontium ferrite and barium ferrite and mixtures thereof, the preferred weight percent of iron will be from 55 to 70 weight percent based on the total weight of iron and strontium and/or barium.

The preferred ferrites are the ferrites having a cubic face-centered configuration, such as the spinels. Ordinarily the ferrites will not be present in the most highly oriented crystalline structure, because it has been found that superior results may be obtained with catalysts wherein the crystalline structure of the ferrites is relatively disordered. A more detailed discussion of these catalyst and their preparation is found in U.S. Pat. No. 4,658,074 which is incorporated herein.

The catalyst compositions useful in the present invention include zinc ferrites containing, as the active components thereof, zinc, iron and oxygen in combination as hereinafter described.

The zinc ferrite constituents of the instant catalyst compositions comprise zinc ferrite of the empirical formula $Zn_xFe_yO_z$ where x will be from about 0.1 to 2, inclusive, and y can be in the range of about 0.3 to 12, inclusive, and z will vary depending upon the number of oxygen vacancies, but will usually be within the range of about 3 to 18, inclusive. Especially preferred are zinc ferrite compositions wherein the ratio of y to x is from about 2:1 to about 5:1. Although the zinc ferrite catalyst may be broadly defined as containing crystalline structures of iron, oxygen and zinc certain type of catalysts are preferred. Zinc ferrite formation may be accomplished by reacting an active compound of iron with an active compound of zinc. By the term active compound is meant a compound which is reactive under the conditions hereinafter described to form the ferrite. The active compounds are suitably oxides or compounds which are converted to oxides during the formation of the ferrite, such as organic and inorganic salts or hydroxides. Active compounds of iron and zinc include the nitrates, hydroxides, hydrates, oxalates, carbonates, acetates, formates, halides, oxides, etc. For example, zinc carbonate may be reacted with iron oxide hydrates to form zinc ferrite. Salts of the desired metals may be co-precipitated and the precipitate heated to form the ferrite. Desired ferrites may be obtained by conducting the reaction to form the ferrite at relatively low temperatures, that is, at temperatures lower than some of the very high temperatures used for the formation of some of the semi-conductor applications. Good results have been obtained by heating the ingredients to a temperature high enough to produce the zinc ferrite, but at conditions no more severe than equivalent to heating to 850° C. for 90 minutes in air. Generally, the maximum temperature will be less than 700° C. and preferably about 650° C. Methods for preparing zinc ferrite catalyst compositions suitable for use in the process of this invention are disclosed in U.S. Patents Nos. 3,270,080; 3,284,536; 3,303,234; 3,303,238; 3,308,182; 3,334,152; 3,420,912; 3,440,299; 3,342,890; 3,450,787; 3,951,869; 3,998,760 and 4,332,972.

As is apparent from the empirical formula presented herein for zinc ferrite, the ratio of iron to zinc in such ferrite mixtures is not restricted to the stoichiometric ratios as would be present in the simple compound zinc ferrite. In these catalyst compositions zinc ferrite compound is present as well as one or more oxides of the constituent cations. For example, if the active compounds are employed such that in the empirical formula y is about 3 and x is 1, the catalyst composition formed therefrom will contain iron oxide in addition to the zinc ferrite formed. Similarly, the zinc ferrite precursor composition may comprise an excess of zinc over the stoichiometric amount to form the ferrite, in which case the resulting catalyst will contain zinc oxide in addition to the zinc ferrite formed.

The preferred zinc ferrite catalyst compositions of the instant invention are those having a face centered cubic structure. However, the zinc ferrites of the will not be present in the most highly oriented crystalline structure because it has been found that superior results may be obtained with catalysts wherein the zinc ferrite is relatively disordered. Such catalyst compositions may be obtained by conducting the reaction to form the zinc ferrite at relatively low temperatures as described herein.

The zinc ferrite catalyst compositions used in the present invention can be identified by their characteristic X-ray diffraction patterns. The preferred catalyst compositions will generally have x-ray diffraction peaks at d-spacings within or about 4.83 to 4.89; 2.95 to 3.01; 2.51 to 2.57; 2.40 to 2.46; 2.08 to 2.14; 1.69 to 1.75; 1.59 to 1.65; and 1.46 to 1.52, with the most intense peak being between 2.51 to 2.57. Particularly preferred catalysts will have d-spacings within or about 4.81 to 4.88; 2.96 to 3.00; 2.52 to 2.56; 2.41 to 2.45; 2.09 to 2.13; 1.70 to 1.74; 1.60 to 1.64; and 1.47 to 1.51, with the most intense peak falling within or about 2.52 to 2.56. These X-ray determinations are suitably run with a cobalt tube.

Although aqueous mediums may generally be employed, when coating a support with the catalyst constituents, it is contemplated that non-aqueous systems can also be employed, if desired, in the preparation of the catalyst. Another suitable method for preparing zinc ferrite composition is by dry-mixing the components.

Catalyst binding agents or fillers not mentioned herein may also be used, but these will not ordinarily exceed about 50 percent or 75 percent by weight of the catalytic surface, and the described catalytic compositions will preferably constitute the main active constituent. These other binding agents and fillers will preferably be essentially inert. Preferred catalysts are those that have as a catalytic surface exposed to the reaction gases at least 25 or preferably 50 weight percent of the defined catalytic surface. The catalytic surface may be introduced as such or it may be deposited on a carrier by methods known in the art such by preparing an aqueous solution or dispersion of a catalytic material and mixing the carrier with the solution or dispersion until the active ingredients are coated on the carrier. If a carrier is utilized, very useful carriers are silicon carbide, aluminum oxide, pumice, and the like. Other known catalyst carriers may be employed When carriers are used, the amount of catalyst on the carrier will suitably be between about 5 to 75 weight percent of the total weight of the active catalytic material plus carrier. Another method for introducing the required surface is to utilize as a reactor a small diameter tube wherein the tube wall is catalytic or is coated with catalytic material. Other methods may be utilized to introduce the catalytic surface such as by the use of rods, wires, mesh, or shreds, and the like, of catalytic material. The catalytic surface described is the surface which is exposed in the dehydrogenation zone to the reaction gases, that is, e.g., if a catalyst carrier is used, the composition described as a catalyst refers to the composition of the surface and not to the total composition of the surface coating plus carrier.

The catalyst compositions of the instant invention may be activated prior to use by treatment with a reducing gas, such as, for example, hydrogen or hydrocarbons. For example, the reduction may be effected with hydrogen at a temperature of from about 500° F. to about 1,000° F. with temperatures of from about 650° F. to about 850° F. being preferred. The time required for reduction will be dependent upon the temperature selected for the reducing step and will generally be from about ten minutes to about two hours.

The catalyst compositions used in this invention may also comprise additives, such as disclosed in U.S. Pat. No. 3,270,080 and U.S. Pat. No. 3,303,238. Phosphorus, silicon, boron, sulfur, or mixtures thereof, are examples of additives. Excellent catalysts may contain less than 5 wt. %, and preferably less than 2 wt. %, of sodium or potassium in the catalyst composition. The catalyst may also comprise other metallic promoters as are well-known in the art.

The Reaction Conditions

The temperature for the dehydrogenation reaction will depend upon the compound being dehydrogenated and the desired level of conversion. Generally, temperatures of from about 500° F. to about 1,200° F. are satisfactory with temperatures of from about 650° F. to about 1,100° F. being preferred.

The amount of oxygen employed in the oxidative dehydrogenation process will vary depending upon the particular compound being dehydrogenated, the number of hydrogen atoms being removed, and the conversion level. For example, in dehydrogenating butane to butene, less oxygen is generally employed than if the reaction were carried out to produce butadiene. Normally oxygen will be supplied in the dehydrogenation zone in an amount from about 0.2 to about 1.0 and preferably from about 0.3 to about 1.2 moles of oxygen per mole of $H_2$ being liberated from the organic compound. Expressed in terms of the organic compound being dehydrogenated, the oxygen is supplied in an amount of from about 0.2 to 2.0 moles per mole of organic compound to be dehydrogenated with a preferred range of from about 0.25 to 1.5 moles of oxygen per mole of organic compound.

Preferably, the reaction mixture contains a quantity of steam or a diluent such as nitrogen. These gases serve to reduce the partial pressure of the organic compound; however, the functions of steam in the reaction are several fold, in that the steam does not act merely as a diluent. Whenever steam is employed in the process of the instant invention, it is employed in an amount generally of from about 2 to about 40 moles of steam per mole of organic compound to be dehydrogenated, with an amount of from about 3 to about 35 moles of steam per mole of organic compound to be hydrogenated being preferred. Especially preferred are amounts of from about 5 to about 30 moles of steam per mole of organic compound to be dehydrogenated. Whenever a diluent is employed instead of steam, such diluents generally may be used in the same quantities as specified for steam.

The process of the instant invention is carried out at atmospheric pressure, superatmospheric pressure or at subatmospheric pressure. The reaction pressure will normally be about or in excess of atmospheric pressure, although subatmospheric pressure may also desirably be used. Generally, the total pressure will be between about 2 p.s.i.a. and about 125 p.s.i.a., with a total pressure of from 4 p.s.i.a. to about 75 p.s.i.a. being preferred. Excellent results are obtained at about atmospheric pressure.

The gaseous reactants may be conducted through the dehydrogenation zone at a fairly wide range of flow rates. The optimum flow rate will depend upon such variables as the temperature and pressure of reaction, and the particular hydrocarbon mix being dehydrogenated. Desirable flow rates may be established by one skilled in the art. Generally, the flow rates will be within the range, of about 0.10 to 15 liquid volumes of the organic compound to be dehydrogenated per volume of dehydrogenation zone containing catalyst per hour designated as liquid hourly space velocity and referred to as LHSV). Usually, the LHSV will be between 0.15 and about 5.0. In calculating space velocities, the volume of a fixed bed dehydrogenation zone containing catalyst is that original void volume of reactor space containing catalyst. The gaseous hourly space velocity (GHSV) is the volume of the hydrocarbon to be dehydrogenated, in the form of vapor calculated under standard conditions of 25° C. and 760 mm. of mercury, per volume of reactor space containing catalyst per hour. Generally, the GHSV will be between about 25 and 6400, and excellent results are obtained between about 38 and 3800. Suitable contact times are, for example, from about 0.001 or higher to about 5 or 10 seconds, with particularly good results being obtained between 0.01 and 3 seconds. The contact time is the calculated dwell time of the reaction mixture in the reaction zone, assuming the moles of product mixture are equivalent to the moles of feed mixture. For the purpose of calculation of residence times, the reaction zone is the portion of the reactor containing catalyst.

The process of this invention is suitably employed with a fixed catalyst bed or a moving catalyst bed, such as a fluidized catalyst bed in the dehydrogenation zone.

The following examples are illustrative only of the invention and are not intended to limit the invention. All percentages are weight percent unless specified otherwise. All conversions, selectivities and yields are expressed in mole percent of the designated feed.

EXAMPLES

Bench scale runs were made using an oxidative dehydrogenation catalyst composition and a catalyst for the removal of acetylenes. The reactor was a 24 inch long, 1 inch I.D. stainless steel tube inserted in a 3100 watt furnace having three separate temperature control elements. The upper 8 inches serves as a steam super heater. The hydrocarbon feed was injected into the super heated steam prior to the steam entering an oxidative dehydrogenation catalyst (Zn ferrite) bed of about 10 inches length. Below the oxidative dehydrogenation catalysts and separated therefrom by a thin bed of inert grain a 5 inch acetylene removal bed is located. The effluent is sampled below the acetylene removal bed. Analyses were by gas-liquid chromatographic methods.

The feed to the oxidative dehydrogenation catalyst is as specified $C_5/C_4$ mix where $C_5=99+\%$ isoamylene $C_4=99+\%$ butene-2, the balance being butadiene and n-butane, the feed contained no acetylenes or carbonyl compounds, LHSV 1.50 over the oxidative dehydrogenation zone, oxygen (fed as air) and steam as indicated in the Tables. The inlet temperature to the oxidative dehydrogenation zone was 660° F. and the temperature in the acetylene removal catalyst zone was about 1000° to 1050° F. Each run was carried out for varying periods with the results given here being taken after several week on stream.

The acetylene removal catalyst used is equivalent to that shown in U.S. Pat. No. 4,658,080 Example 15. This is zinc ferrite similar to the oxidative dehydrogenation catalyst, but additionally containing nickel and barium components. The acetylene removal catalyst is essentially invisible in the process, that is, there is substantially no change in the conversion, selectivity or yield of the oxidative dehydrogenation product, e.g., isoprene, only the removal of the acetylenes. Catalysts were pretreated in situ by reduction for 2 hours at 950° F. in the presence of a fluent gas consisting of steam and hydrogen. Steam was passed over the catalyst at a GHSV of 10 times the hydrocarbon feed rate to be employed and the hydrogen rate was 400 cc./min.

The catalyst compositions described and pre-treated according to the procedure in Part A of this example were used to oxidatively dehydrogenate feed as specified in the Tables. The operating data and results are given in the following Tables. The data in TABLE I and TABLE II is the same, but arranged in different order to better demonstrate the invention and the improved oxidative dehydrogenation of amylene. In TABLE I the data is grouped by $C_4/C_5$ ratios, and in TABLE II the data is grouped by run conditions (steam to HC ratio and oxygen to HC ratio).

TABLE 1

| | | | | | | | | | | | |
|---|---|---|---|---|---|---|---|---|---|---|---|
| | | | C4/C5 Bench Tests 1.5 LHSV | | | | | | | | |
| C4/C5 Feed Ratio | Steam To HC Ratio | Oxygen To HC Ratio | MOLE % C5 | | | MOLE % C4 | | | Wt. Avg. C4 C5 Yield | Wt % IP In C5-Cut | Wt % BD IN C4 Cut |
| | | | Conv. | Sel. | Yield | Conv. | Sel | Yield | | | |
| 0/100 | 20/1 | .55 | 46.6 | 89.5 | 41.7 | — | — | — | — | 43.1 | — |
| 0/100 | 20/1 | .60 | 47.6 | 89.0 | 42.4 | — | — | — | — | 43.8 | — |
| 0/100 | 20/1 | .65 | 49.0 | 87.6 | 42.9 | — | — | — | — | 44.8 | — |
| 0/100 | 20/1 | .70 | 46.6 | 84.0 | 39.1 | — | — | — | — | 41.3 | — |
| 40/60 | 15/1 | .55 | 44.8 | 83.6 | 37.5 | 13.2 | 71.8 | 9.5 | 26.3 | 39.5 | 10.4 |
| 40/60 | 15/1 | .60 | 46.7 | 82.0 | 38.3 | 13.3 | 77.3 | 10.3 | 27.1 | 40.9 | 11.1 |
| 40/60 | 15/1 | .65 | 49.3 | 77.3 | 38.1 | 12.4 | 94.6 | 11.7 | 27.5 | 42.0 | 12.2 |
| 40/60 | 15/1 | .70 | 49.7 | 77.3 | 38.4 | 15.0 | 82.7 | 12.4 | 28.0 | 42.4 | 13.0 |
| 40/60 | 20/1 | .55 | 50.7 | 79.8 | 40.5 | 11.3 | 103.0 | 11.6 | 28.9 | 44.1 | 12.0 |
| 40/60 | 20/1 | .60 | 50.3 | 79.3 | 39.9 | 11.4 | 100.4 | 11.4 | 28.5 | 43.6 | 11.8 |

TABLE 1-continued

C4/C5 Bench Tests
1.5 LHSV

| C4/C5 Feed Ratio | Steam To HC Ratio | Oxygen To HC Ratio | MOLE % C5 Conv. | Sel. | Yield | MOLE % C4 Conv. | Sel | Yield | Wt. Avg. C4 C5 Yield | Wt % IP In C5-Cut | Wt % BD IN C4 Cut |
|---|---|---|---|---|---|---|---|---|---|---|---|
| 40/60 | 20/1 | .65 | 46.0 | 88.4 | 40.7 | 19.7 | 50.6 | 10.0 | 28.4 | 42.0 | 11.6 |
| 40/60 | 20/1 | .70 | 58.2 | 74.7 | 43.5 | 11.2 | 137.4 | 15.4 | 32.3 | 50.0 | 14.8 |
| 60/40 | 15/1 | .55 | 58.2 | 73.5 | 42.8 | 18.0 | 84.0 | 15.1 | 26.2 | 50.0 | 15.7 |
| 60/40 | 15/1 | .60 | 58.3 | 74.1 | 43.2 | 18.2 | 80.3 | 14.6 | 26.0 | 49.9 | 15.4 |
| 60/40 | 15/1 | .65 | 60.5 | 73.6 | 44.5 | 21.9 | 80.2 | 17.5 | 28.3 | 51.9 | 18.3 |
| 60/40 | 15/1 | .70 | 60.6 | 72.3 | 43.8 | 22.1 | 70.0 | 15.5 | 26.8 | 51.5 | 16.6 |
| 60/40 | 20/1 | .55 | 56.4 | 79.9 | 45.1 | 16.2 | 76.4 | 12.3 | 25.4 | 49.6 | 13.1 |
| 60/40 | 20/1 | .60 | 59.7 | 78.4 | 46.8 | 17.7 | 78.6 | 13.9 | 27.1 | 52.6 | 14.7 |
| 60/40 | 20/1 | .65 | 61.6 | 74.1 | 45.6 | 18.3 | 80.2 | 14.7 | 27.1 | 56.4 | 15.4 |
| 60/40 | 20/1 | .70 | 66.7 | 73.7 | 49.2 | 23.1 | 85.1 | 19.7 | 31.5 | 58.4 | 20.1 |
| 80/20 | 15/1 | .55 | 67.2 | 67.3 | 45.2 | 20.9 | 85.0 | 17.7 | 23.2 | 56.0 | 18.2 |
| 80/20 | 15/1 | .60 | 71.3 | 68.7 | 49.0 | 27.0 | 84.5 | 22.8 | 28.0 | 60.9 | 23.3 |
| 80/20 | 15/1 | .65 | 73.9 | 64.1 | 47.3 | 29.9 | 85.9 | 25.6 | 29.9 | 62.3 | 26.0 |
| 80/20 | 15/1 | .70 | 76.2 | 60.9 | 46.4 | 32.4 | 81.3 | 26.3 | 30.3 | 63.5 | 26.8 |
| 80/20 | 20/1 | .55 | 76.4 | 76.1 | 58.2 | 27.7 | 82.3 | 22.8 | 29.9 | 69.3 | 23.1 |
| 80/20 | 20/1 | .60 | 77.8 | 74.3 | 57.8 | 29.5 | 80.0 | 23.6 | 30.4 | 70.2 | 24.3 |
| 80/20 | 20/1 | .65 | 80.5 | 71.1 | 57.3 | 31.2 | 86.3 | 27.0 | 33.1 | 72.4 | 27.3 |
| 80/20 | 20/1 | .70 | 77.8 | 68.1 | 53.0 | 30.3 | 77.8 | 23.6 | 29.5 | 67.7 | 24.6 |
| 100/0 | 15/1 | .55 | | | | 62.0 | 92.0 | 57.0 | | | 58.0 |

TABLE II

C4/C5 Bench Tests
1.5 LHSV

| C4/C5 Feed Ratio | Steam To HC Ratio | Oxygen To HC Ratio | MOLE % C5 Conv. | Sel. | Yield | MOLE % C4 Conv. | Sel | Yield | Wt. Avg. C4 C5 Yield | Wt % IP In C5-Cut | Wt % BD IN C4 Cut |
|---|---|---|---|---|---|---|---|---|---|---|---|
| 0/100 | 20/1 | .55 | 46.6 | 89.5 | 41.7 | — | — | — | — | 43.1 | — |
| 40/60 | 20/1 | .55 | 50.7 | 79.8 | 40.5 | 11.3 | 103.0 | 11.6 | 28.9 | 44.1 | 12.0 |
| 60/40 | 20/1 | .55 | 56.4 | 79.9 | 45.1 | 16.2 | 76.4 | 12.3 | 25.4 | 49.6 | 13.1 |
| 80/20 | 20/1 | .55 | 76.4 | 76.1 | 58.2 | 27.7 | 82.3 | 22.8 | 29.9 | 69.3 | 23.1 |
| 0/100 | 20/1 | .60 | 47.6 | 89.0 | 42.4 | — | — | — | — | 43.8 | — |
| 40/60 | 20/1 | .60 | 50.3 | 79.3 | 39.9 | 11.4 | 100.4 | 11.4 | 28.5 | 43.6 | 11.8 |
| 60/40 | 20/1 | .60 | 59.7 | 78.4 | 46.8 | 17.7 | 78.6 | 13.9 | 27.1 | 52.6 | 14.7 |
| 80/20 | 20/1 | .60 | 77.8 | 74.3 | 57.8 | 29.5 | 80.0 | 23.6 | 30.4 | 70.2 | 24.3 |
| 0/100 | 20/1 | .65 | 49.0 | 87.6 | 42.9 | — | — | — | — | 44.8 | — |
| 40/60 | 20/1 | .65 | 46.0 | 88.4 | 40.7 | 19.7 | 50.6 | 10.0 | 28.4 | 42.0 | 11.6 |
| 60/40 | 20/1 | .65 | 61.6 | 74.1 | 45.6 | 18.3 | 80.2 | 14.7 | 27.1 | 56.4 | 15.4 |
| 80/20 | 20/1 | .65 | 80.5 | 71.1 | 57.3 | 31.2 | 86.3 | 27.0 | 33.1 | 72.4 | 27.3 |
| 0/100 | 20/1 | .70 | 46.6 | 84.0 | 39.1 | — | — | — | — | 41.3 | — |
| 40/60 | 20/1 | .70 | 58.2 | 74.7 | 43.5 | 11.2 | 137.4 | 15.4 | 32.3 | 50.0 | 14.8 |
| 60/40 | 20/1 | .70 | 66.7 | 73.7 | 49.2 | 23.1 | 85.1 | 19.7 | 31.5 | 58.4 | 20.1 |
| 80/20 | 20/1 | .70 | 77.8 | 68.1 | 53.0 | 30.3 | 77.8 | 23.6 | 29.5 | 67.7 | 24.6 |
| 40/60 | 15/1 | .55 | 44.8 | 83.6 | 37.5 | 13.2 | 71.8 | 9.5 | 26.3 | 39.5 | 10.4 |
| 60/40 | 15/1 | .55 | 58.2 | 73.5 | 42.8 | 18.0 | 84.0 | 15.1 | 26.2 | 50.0 | 15.7 |
| 80/20 | 15/1 | .55 | 67.2 | 67.3 | 45.2 | 20.9 | 85.0 | 17.7 | 23.2 | 56.0 | 18.2 |
| 100/0 | 15/1 | .55 | | | | 62.0 | 92.0 | 57.0 | | | 58.0 |
| 40/60 | 15/1 | .60 | 46.7 | 82.0 | 38.3 | 13.3 | 77.3 | 10.3 | 27.1 | 40.9 | 11.1 |
| 60/40 | 15/1 | .60 | 58.3 | 74.1 | 43.2 | 18.2 | 80.3 | 14.6 | 26.0 | 49.9 | 15.4 |
| 80/20 | 15/1 | .60 | 71.3 | 68.7 | 49.0 | 27.0 | 84.5 | 22.8 | 28.0 | 60.9 | 23.3 |
| 40/60 | 15/1 | .65 | 49.3 | 77.3 | 38.1 | 12.4 | 94.6 | 11.7 | 27.5 | 42.0 | 12.2 |
| 60/40 | 15/1 | .65 | 60.5 | 73.6 | 44.5 | 21.9 | 80.2 | 17.5 | 28.3 | 51.9 | 18.3 |
| 80/20 | 15/1 | .65 | 73.9 | 64.1 | 47.3 | 29.9 | 85.9 | 25.6 | 29.9 | 62.3 | 26.0 |
| 40/60 | 15/1 | .70 | 49.7 | 77.3 | 38.4 | 15.0 | 82.7 | 12.4 | 28.0 | 42.4 | 13.0 |
| 60/40 | 15/1 | .70 | 60.6 | 72.3 | 43.8 | 22.1 | 70.0 | 15.5 | 26.8 | 51.5 | 16.6 |
| 80/20 | 15/1 | .70 | 76.2 | 60.9 | 46.4 | 32.4 | 81.3 | 26.3 | 30.3 | 63.5 | 26.8 |

The invention claimed is:

1. A process for the oxidative dehydrogenation of aliphatic hydrocarbons having five carbon atoms comprising contacting a mixture of $C_5$ aliphatic hydrocarbons and from 15 to 95 mole % $C_4$ aliphatic hydrocarbons based on the total $C_5$ and $C_4$ aliphatic hydrocarbons with an oxidative dehydrogenation catalyst comprising zinc ferrite in the presence of oxygen and steam.

2. The process according to claim 1 wherein said mixture contains at least 20 mole % $C_4$ aliphatic hydrocarbons.

3. The process according to claim 1 wherein said mixture contains up to 80 mole % $C_4$ aliphatic hydrocarbons.

4. The process according to claim 1 wherein said mixture contains from 20 to 80 mole % $C_4$ aliphatic hydrocarbons.

5. The process according to claim 1 wherein said mixture contains 30 to 90 mole % $C_4$ aliphatic hydrocarbons.

6. The process according to claim 5 wherein said mixture contains 40 to 80 mole % $C_4$ aliphatic hydrocarbons.

7. The process according to claim 6 wherein said mixture contains 50 to 70 mole % C4 aliphatic hydrocarbons.

8. The process according to claim 1 wherein said $C_5$ aliphatic hydrocarbons comprises amylenes.

9. The process according to claim 8 wherein said $C_4$ aliphatic hydrocarbons comprises butenes.

10. The process according to claim 9 wherein said amylenes comprise isoamylenes.

11. The process according to claim 10 wherein the amount of oxygen is from about 0.2 to 1.0 moles per mole of $H_2$ being liberated from hydrocarbons in the oxidative dehydrogenation and from about 2 to 40 moles of steam per mole of hydrocarbons to be dehydrogenated.

12. The process according to claim 11 wherein the liquid hourly space velocity of said hydrocarbons is in the range of 0.10 to 15.

13. In a process for the preparation of isoprene by contacting isoamylenes with an oxidative dehydrogenation catalyst comprising zinc ferrite in the presence of oxygen and steam at a temperature in the range 500° to 1,200° F. wherein the improvement comprises cofeeding from 30 to 90 mole % butenes with said isoamylenes, based on the total of butenes and isoamylenes.

14. The process according to claim 13 wherein said mixture contains 40 to 80 mole % C4 aliphatic hydrocarbons.

15. The process according to claim 14 wherein said mixture contains 50 to 70 mole % C4 aliphatic hydrocarbons.

16. The process according to claim 15 wherein the amount of oxygen is from about 0.2 to 1.0 moles per mole of $H_2$ being liberated from hydrocarbons in the oxidative dehydrogenation and from about 2 to 40 moles of steam per mole of hydrocarbons to be dehydrogenated.

17. The process according to claim 16 wherein the liquid hourly space velocity of said hydrocarbons is in the range of 0.10 to 15.

18. A process for the oxidative dehydrogenation of isoamylenes comprising contacting a mixture of isoamylenes and from 30 to 70 mole % butenes based on the total isoamylenes and butenes with a zinc ferrite oxidative dehydrogenation catalyst in the presence of oxygen and steam.

19. The process according to claim 18 wherein said mixture contains 50 to 70 mole % C4 aliphatic hydrocarbons.

20. The process according to claim 19 wherein the amount of oxygen is from about 0.2 to 1.0 moles per mole of $H_2$ being liberated from hydrocarbons in the oxidative dehydrogenation and from about 2 to 40 moles of steam per mole of hydrocarbons to be dehydrogenated.

21. The process according to claim 20 wherein the liquid hourly space velocity of said hydrocarbons is in the range of 0.10 to 15.

* * * * *